United States Patent [19]

Kawamatsu et al.

[11] 4,443,246

[45] Apr. 17, 1984

[54] HERBICIDAL PYRIDYL-ETHOXY-PHENYL UREA DERIVATIVES

[75] Inventors: Yutaka Kawamatsu, Kyoto; Takahiro Saraie, Toyono; Harutoshi Yoshikawa, Yawata, all of Japan

[73] Assignee: Takeda Chemical Industries, Ltd., Osaka, Japan

[21] Appl. No.: 385,857

[22] Filed: Jun. 7, 1982

[30] Foreign Application Priority Data

Jun. 16, 1981 [JP] Japan ................... 56-93549

[51] Int. Cl.$^3$ ................ A01N 43/40; C07D 213/86
[52] U.S. Cl. ...................................... 71/94; 546/332
[58] Field of Search ........................... 546/332; 71/94

[56] References Cited

U.S. PATENT DOCUMENTS

```
3,931,200  1/1976  Gulbenk ................ 546/305
3,991,068 11/1976  Gulbenk ................ 546/337
4,028,092  6/1977  Gulbenk ................ 71/94
```

OTHER PUBLICATIONS

Smith, The Chemistry of Open-Chain Organic Nitrogen Compounds, vol. I, pp. 275-276, Benjamin Pub. (1965).
Sidgwick et al., The Organic Chemistry of Nitrogen, vol. I, Oxford Univ. Press, pp. 428-429 (1966).
Chemical Abstracts, vol. 96, No. 11, item No. 85423v, Mar. 15, 1982.
Chemical Abstracts, vol. 97, No. 15, item No. 127,508e Oct. 11, 1982.

*Primary Examiner*—Alan L. Rotman
*Attorney, Agent, or Firm*—Wenderoth, Lind & Ponack

[57] ABSTRACT

Urea derivatives of the general formula:

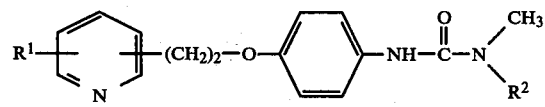

wherein $R^1$ stands for a lower alkly group; and $R^2$ stands for a lower alkyl group or a lower alkoxy group, or a salt thereof, are novel and have a strong herbicidal activity against various species of weeds and shows a very low phytotoxicity to crop plants.

5 Claims, No Drawings

HERBICIDAL PYRIDYL-ETHOXY-PHENYL UREA DERIVATIVES

The present invention relates to new urea derivatives having herbicidal activity. It has been known that urea derivatives, for example N'-[4-(4-chlorophenoxy)-phenyl]-N,N-dimethylurea (Common name: chloroxuron), have herbicidal activity. Further in U.S. Pat. Nos. 3,931,200, 3,991,068 and 4,028,092 it was reported that some urea derivatives including (substituted pyridinyl)-methoxy- or 1-(substituted pyridinyl)ethoxy-phenyl urea derivatives were useful as herbicides. But they are not necessarily satisfactory in selectivity between weeds and crop plants, and exploitation of a herbicidal agent having higher selectivity has been desired.

The present inventors carried out research work for finding out an improved herbicide having less phytotoxicity and higher selectivity. As a result, the present inventors found that a compound of the general formula [I]:

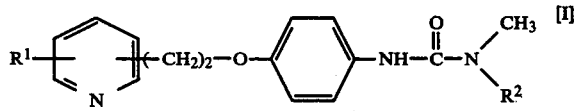

wherein $R^1$ stands for a lower alkyl group; and $R^2$ stands for a lower alkyl group or a lower alkoxy group, or a salt thereof, have a strong herbicidal activity against various species of weeds and shows very low phytotoxicity to crop plants such as corn, and their further various studies resulted in accomplishment of the present invention. In the above general formula [I], $R^1$ stands for a lwoer alkyl group of 1 to 4 carbon atoms, e.g. methyl, ethyl, propyl, isopropyl, butyl, sec-butyl or tert-butyl. One or two of these groups may occupy an optional position or positions as a substituent or substituents on the pyridine ring. And, the position on the pyridine ring at which the substituted phenoxyalkylene and the pyridine ring are combined is optional. $R^2$ stands for a lower alkyl group of 1 to 4 carbon atoms, e.g. methyl, ethyl, propyl, isopropyl, butyl, sec-butyl or tert-butyl; and a lower alkoxy group of 1 to 4 carbon atoms, e.g. methoxy, ethoxy, propoxy, isopropoxy, butoxy, sec-butoxy or tert-butoxy. Preferably $R^1$ is methyl or ethyl and $R^2$ is methyl or methoxy.

Examples of the compound of the general formula [I] include:
N,N-dimethyl-N'-[4-[2-(6-methyl-2-pyridyl)ethoxy]-phenyl]urea,
N,N-dimethyl-N'-[4-[2-(5-methyl-2-pyridyl)ethoxy]-phenyl]urea,
N,N-dimetnyl-N'-[4-[2-(4-methyl-2-pyridyl)ethoxy]-phenyl]urea,
N,N-dimethyl-N'-[4-[2-(3-methyl-2-pyridyl)ethoxy]-phenyl]urea,
N,N-dimethyl-N'-[4-[2-(4,6-dimethyl-2-pyridyl)ethoxy]phenyl]urea,
N,N-dimethyl-N'-[4-[2-(5-ethyl-2-pyridyl)ethoxy]-phenyl]urea,
N,N-dimethyl-N'-[4-[2-(6-ethyl-2-pyridyl)ethoxy]-phenyl]urea,
N,N-dimethyl-N'-[4-[2-(6-ethyl-5-methyl-2-pyridyl)ethoxy]phenyl]urea,
N-methoxy-N-methyl-N'-[4-[2-(6-methyl-2-pyridyl)ethoxy]phenyl]urea,
N-methoxy-N-methyl-N'-[4-[2-(5-methyl-2-pyridyl)ethoxy]phenyl]urea,
N-methoxy-N-methyl-N'-[4-[2-(4-methyl-2-pyridyl)ethoxy]phenyl]urea,
N-methoxy-N-methyl-N'-[4-[2-(3-methyl-2-pyridyl)ethoxy]phenyl]urea,
N'-[4-[2-(4,6-dimethyl-2-pyridyl)ethoxy]phenyl]-N-methoxy-N-methylurea,
N'-[4-[2-(5-ethyl-2-pyridyl)ethoxy]phenyl]-N-methoxy-N-methylurea,
N'-[4-[2-(6-ethyl-2-pyridyl)ethoxy]phenyl]-N-methoxy-N-methylurea, and the like.

The present invention includes salts of the compound [I] with an inorganic acid such as hydrochloric acid, surfuric acid or phosphoric acid, or with an organic acid such as p-toluenesulfonic acid, formic acid, acetic acid, propionic acid, tartaric acid, malic acid, succinic acid or fumaric acid.

In case of using the compound of the present invention as a herbicide, use is made of one or more species of the compounds of the present invention, depending on purposes, by dissolving in a suitable liquid carrier (e.g. a solvent) or by dispersing in it, or by mixing with a suitable solid carrier (e.g. a diluent or a filler) or by allowing same to be absorbed on the carrier, and, upon necessity, by further adding an emulsifier, suspending agent, extender, penetrating agent, wetting agent, viscosity builder, stabilizer or the like, thereby to prepare an oil solution, emulsifiable concentrate, wettable powder, dust, granule, tablet, aerosol, ointment or the like.

These preparations can be formulated by a per se known manner. The concentrations of the active ingredients in liquid compositions and wettable powders are suitably from about 10 to about 90 weight %. In dusts, the concentration of the active ingredients can be from about 0.1 to about 10 weight %. The concentration of the active ingredients in granules are generally from about 1 to about 20 weight %. These ranges of the concentration may be extended adequately depending upon purposes. The emulsifiable concentrate or wettable powders are usually applied after dilution with adequate volume of water (e.g. 100 to 100,000 times).

Suitable examples of liquid carriers (solvents) to be used for the herbicide include water, alcohols (e.g., methyl alcohol, ethyl alcohol or ethylene glycol), ketones (e.g., acetone or ethyl methyl ketone), ethers (e.g. dioxane, tetrahydrofuran or cellosolve), aliphatic hydrocarbons (e.g., gasoline, kerosene, fuel oil or machine oil), aromatic hydrocarbons, (e.g., benzene, toluene, xylene, solvent naphtha or methyl naphthalene), halogenated hydrocarbons (e.g., chloroform or carbon tetrachloride), acid amides (e.g., dimethylformamide), esters (ethyl acetate, butyl acetate or a glyceride of a fatty acid) or nitriles (e.g., acetonitrile), and use is made of any one of them or a mixture of two or more of them.

Examples of solid carriers (a diluent, or a filler) include vegetable powder (e.g., soybean flour, tobacco leaf powder, wheat flour or saw-dust), mineral powder (e.g. clays such as kaoline, bentonite or acid clay, talc such as tale powder or agalmalotile, or silicas such as diatomaceous earth or mica powder) as well as alumina, powdery sulfur and activated charcoal, and use is made of any one species of them or a mixture of two or more of them.

Examples of ointment bases include polyethylene glycol; pectin; a polyhydric alcohol ester of a higher fatty acid, e.g., monostearic acid glycerine ester; cellulose derivatives, e.g., methyl cellulose; sodium alginate;

bentonite; higher alcohols; polyhydric alcohols, e.g., glycerine; vaseline; white vaseline; fluid vaseline; lard; various vegetable oils; lanolin; dehydrated lanolin; hardened oil; waxes; or resins. These materials may be employed alone or as a mixture, or as supplemented by surfactants or/and other materials.

As the surfactants which are used, upon necessity, as emulsifiers, spreaders, penetrants, dispersing agents, etc., use is made of soaps, polyoxyalkyl aryl esters (e.g., Nonal® manufactured by Takemoto Oils & Fats Co., Japan), alkyl sulfates (e.g, Emal 10®, Emal 40® manufactured by Kao Atlas Co., Japan), alkyl sulfonates (e.g., Neogen®, Neogen T® manufactured by Daiichi Seiyaku Kogyo Co., Japan: Neopelex® manufactured by Kao Atlas Co., Japan), polyethylene glycol ethers (e.g., Nonipol 85®, Nonipol 100®, Nonipol 160®, manufactured by Sanyo Chemical Industries, Japan), polyhydric alcohol esters (e.g., Tween 20®, Tween 80® manufactured by Kao Atlas Co., Japan).

In utilizing the compounds (I) as herbicides, their application rate is about 1 to 50 g., preferably about 2 to 40 g per are of a upland field, and about 1 to 50 g., preferably about 2 to 40 g., per are of a paddy field. It is suitable to use the compounds of the present invention as a post-emergence herbicide.

The compound of the present invention shows lowered toxicity to mammals and fishes. For example, the $LD_{50}$ value of N,N-dimethyl-N'-[4-[2-(6-methyl-2-pyridyl)ethoxy]phenyl]urea, is not lower than 300 mg/kg (orally in mice), and the TLm value is not lower than 10 ppm (pink cryprinodont), and can be safely uses as agricultural drugs. Additionally, the compounds of the present invention can be used as mixtures by formulating a herbicide containing the compound of the present invention with other kinds of herbicides, plant growth regulators, fungicides (e.g., organochlorine fungicides, organosulfur fungicides, antibiotics, etc.), insecticides (e.g., organophosphorus insecticides, nonsynthetic insecticides, etc.), miticides, nematocides, synergists, attractants, repellents, pigments, fertilizers, etc.

The compound of the present invention is prepared by allowing a compound of the general formula [II]:

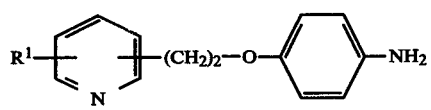

wherein $R^1$ stands for a lower alkyl group as defined above, to react with a compound of the general formula [III]:

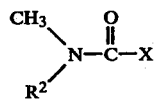

wherein $R^2$ stands for a lower alkyl group or a lower alkoxy group as defined above; X stands for a halogen e.g. fluorine, chlorine, bromine or iodine.

This reaction may, in general, be conducted in the presence of a solvent, for example, hydrocarbons such as benzene, toluene, xylene, ligroin or hexane; ethers such as ethylether, isopropylether, tetrahydrofuran, dioxane, ethyleneglycol dimethylether or methyl cellosolve; halogenated hydrocarbons such as chloroform, carbon tetrachloride or dichloromethane; dimethylformamide; dimethylsulfoxide, acetonitrile or ethyl acetate. These solvents may be used singly or in combustion of two of them in a suitable ratio, for example, 1:1 to 1:10 (by weight), or in combination of three or more of them. When a mixture solvent is not of homogeneous phase, the reaction may be conducted in the presence of a phase transfer catalyst (e.g., tetra-n-butylammonium bromide).

This reaction may be carried out in the presence of inorganic or organic bases such as alkali metal hydrogen carbonates (e.g., sodium hydrogen carbonate etc.), alkali metal carbonates (e.g. sodium carbonate, potassium carbonate, etc.) alkali metal hydroxides (e.g. potassium hydroxide, sodium hydroxide, etc.), trimethylamine, triethylamine, tributylamine, N-methylmorpholine, N-methylpiperidine, N,N-dimethylaniline, pyridine, picoline or lutidine. The above exemplified organic bases can be employed per se as solvents.

The compound [III] is usually used in a molar ratio of 1 relative to the starting compound [II], but, depending on cases, the ratio varies within the range of from 1:5 to 5:1.

The reaction is usually conducted at a temperature ranging from ice-cooling to 120° C., preferably 10° to 50° C. The reaction time may be suitably determined relatively to the reaction temperature then employed, and it ranges from several minutes to several ten hours, preferably from 0.5 hour to 3 hours.

The compound of the present invention can also be prepared by allowing a compound of the general formula [IV]:

wherein Y and Y' respectively stand for a halogen or a nitrogen-containing aromatic five-membered ring residue, to react with a compound [II] and a compound of the general formula [V]:

wherein $R^2$ stands for a lower alkyl group or a lower alkoxy group as defined above.

In the above general formula [IV], Y and Y' respectively stand for a halogen, e.g. chlorine, bromine or iodine; or a nitrogen-containing aromatic five-membered ring residue which may be substituted by one to three lower alkyl groups of 1 to 4 carbon atoms, e.g. methyl, ethyl, propyl or butyl; or one phenyl. Examples of the nitrogen-containing aromatic five-membered ring residue include triazolyl, (e.g. 1,2,4-triazolyl, 1,2,3-triazolyl etc.) benzotriazolyl, imidazolyl, benzimidazolyl pyrazolyl, indazolyl and so on.

Preferred examples of the compound [IV] above include phosgene, 1,1'-carbonyldi-(1,2,4-triazole), 1,1'-carbonyldiimidazole, 1,1'-carbonyldibenzotriazole, 1,1'-carbonylbenzimidazole, 1,1'-carbonylbis-(3,5-dimethylpyrazole), 1,1'-carbonyldipyrazole, 1,1'-carbonylbis-(2-methylimidazole), 1,1'-carbonyldiindazole or 1,1'-carbonylbis-(2-phenylimidazole), etc.

The reaction of a compound [IV] with a compound [II] and a compound [V] is conducted in the presence of an inert solvent, e.g. benzene, toluene, xylene, chloroform, acetonitrile, dichloromethane, tetrahydrofuran, acetone, ethyl acetate, dimethylsulfoxide, dimethylformamide, hexamethyl phosphoric triamide, etc., singly or as a mixture of two or more of them. The reaction temperature ranges generally from −20° C. to 40° C., and preferably from −10° C. to 20° C. Usually the reaction proceeds smoothly at these conditions and completes in about 0.5 to 3 hours, typically in 1 to 2 hours. About equimolar amounts of each of a compound [II] and a compound [V] relative to a compound [IV] is used preferably, but the use of them in the range of about 1.1 to 2.0 times as much as a compound [IV] does not give an adverse effect on the reaction.

This reaction may be carried out in the presence of organic bases such as triethylamine, tributylamine, N-methylpiperidine, -N-methylmorpholine, N,N-dimethylaniline, pyridine, picoline, lutidine or collidine, or inorganic bases such as alkalimetal hydrogen carbonates (e.g. sodium hydrogen carbonate, potassium hydrogen carbonate) or alkalimetal carbonates (e.g. sodium carbonate, potassium carbonate).

When the compound of the present invention is obtained in the free form [I], it can be converted into the corresponding salt according to the per se known procedure, and vice versa.

The compound of the present invention prepared in the above manner can be isolated and purified by such known procedures as concentration, concentration under reduced pressure, distillation, fractional distillation, solvent extraction, pH adjustment, phase transfer, chromatography, crystallization and recrystallization.

The compound [II] employed as a starting material in the present invention can be prepared according to the known procedures. (e.g. Japanese published unexamined patent application No. 115344/1979)

Further, the starting compound [II] can be obtained by the reaction schema as below.

Schema

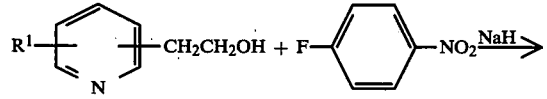

-continued
Schema

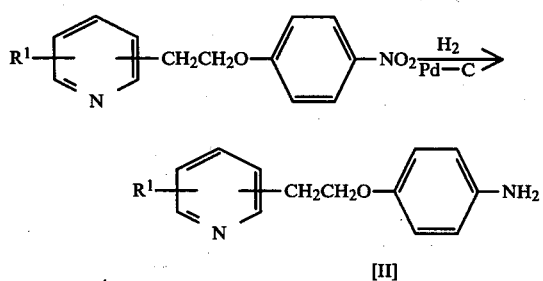

[In the formula, R¹ is as defined above].

The starting compound [IV] can be prepared in accordance with the known procedures.

For example, the compound [IV] (wherein Y and Y' respectively stand for a nitrogen-containing aromatic five-membered ring residue] can be obtained by allowing phosgene to react with a nitrogen-containing aromatic five-membered cyclic compound.

The starting compounds [III] and [V] can be prepared in accordance with the procedures of a known method.

Below described are Reference Examples, Examples and Test Examples to illustrate in detail the contents of the present invention. Symbols used in the examples mean as follows, respectively. s: singlet, d: doublet, t: triplet, m: multiplet, br.s: broad singlet.

REFERENCE EXAMPLE 1

4-[2-(6-methyl-2-pyridyl)ethoxy]nitrobenzene

To a solution of 15 g of 2-(6-methyl-2-pyridyl)ethanol and 15.5 g of 4-fluoronitrobenzene in 200 ml of dimethylformamide is added, while stirring on ice bath, 4.8 g of sodium hydride (60% in oil) in limited amounts. The mixture is stirred for 30 minutes and then poured into 1.5 l of ice-water.

The separated crystals are collected by filtration and recrystallized from methanol to give 20 g of 4-[2-(6-methyl-2-pyridyl)ethoxy]nitrobenzene as colorless crystals, mp 61° to 62° C.

Elemental Analysis, for $C_{14}H_{14}N_2O_3$: Calcd. (%): C, 65.11; H, 5.46; N, 10.85. Found (%): C, 64.95; H, 5.82; N, 10.56.

By a procedure analogous to that in Reference Example 1, following compounds are prepared.

| Compound | Physico-chemical constant |
|---|---|
| CH₃-pyridyl-CH₂CH₂-O-phenyl-NO₂ | IR(nujol) $\nu_{max}^{cm-1}$: 1375, 1500, 1240 |
| CH₃-pyridyl-CH₂CH₂-O-phenyl-NO₂ | IR(nujol) $\nu_{max}^{cm-1}$: 1370, 1510, 1240 |

| Compound | Physico-chemical constant |
|---|---|
| 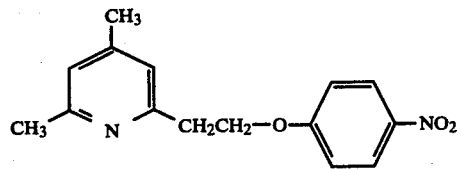 | mp 77 to 79° C. |
| 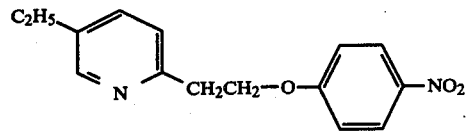 | mp 55 to 58° C. |
| 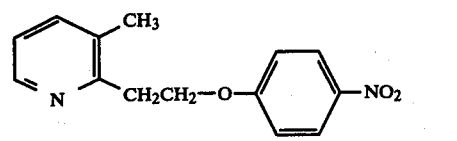 | mp 110 to 111° C. |

REFERENCE EXAMPLE 2

4-[2-(6-methyl-2-pyridyl)ethoxy]aniline

To a solution of 2.8 g of 4-[2-(6-methyl-2-pyridyl)ethoxy]nitrobenzene in the mixture consisting of 30 ml of methanol and 20 ml of ethyl acetate is added 0.5 g of 10% palladium carbon, and then the mixture is shaken in a stream of hydrogen. After absorption of hydrogen ceased, the mixture is filtered and the filtrate is concentrated under reduced pressure. The residue is dissolved in ethyl acetate and washed with water, dried over anhydrous magnesium sulfate and then concentrated to give 2.24 g of 4-[2-(6-methyl-2-pyridyl)ethoxy]aniline as yellowish brown powder.

NMR(CDCl$_3$)  δ:  2.45(3H,s),  3.11(2H,t), 3.50(2H,br.s), 4.20(2H,t), 6.5 to 7.10(7H,m).

By a procedure analogous to that in Reference Example 2, following compounds are prepared.

| Compound | Physico-chemical constant |
|---|---|
| 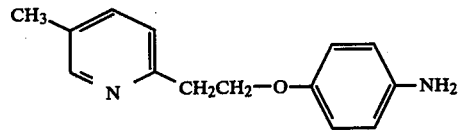 | NMR(CDCl$_3$)δ, ppm: 2.20(3H,s), 3.10(2H,t), 3.40(2H,br.s), 4.17(2H,t), 6.38–8.30(7H,m) |
| 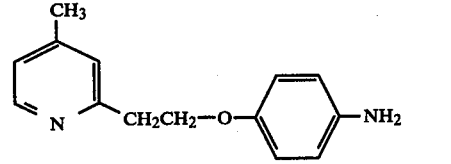 | NMR(CDCl$_3$)δ, ppm: 2.24(3H,s), 3.13(2H,t), 2.5(2H,br.s), 4.22(2H,t), 6.60–7.20(6H,m), 8.27(1H,d) |
| 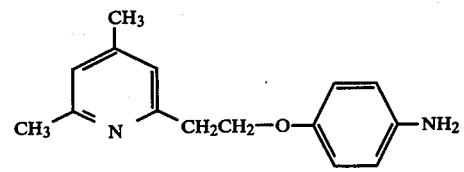 | NMR(CDCl$_3$)δ, ppm: 2.22(3H,s), 2.46(3H,s), 3.11(2H,t), 3.51(2H,br.s), 4.20(2H,t), 6.38–7.00(6H,m) |
| 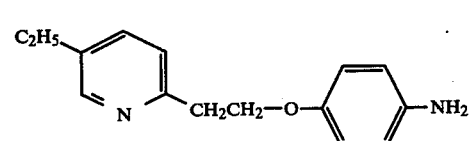 | mp 36 to 38° C. |

| Compound | Physico-chemical constant |
|---|---|
| [structure: 3-methyl-2-pyridyl-CH₂CH₂-O-C₆H₄-NH₂] | mp 102 to 104° C. |

EXAMPLE 1

N,N-dimethyl-N'-[4-[2-(6-methyl-2-pyridyl)ethoxy]-phenyl]urea

To a homogeneous solution of 2.2 g of 4-[2-(6-methyl-2-pyridyl)ethoxy]aniline in 20 ml of pyridine is added 2.2 g of dimethylcarbamoyl chloride at room temperature, then the mixture is stirred for one hour at 80° C. The reaction mixture is subjected to extraction with ethyl acetate, and the extract is washed with water. The washed extract is dried over anhydrous magnesium sulfate, followed by concentration to leave a crude product, which is recrystallized from a mixture of ethyl acetate and cyclohexane to yield 2.0 g of N,N-dimethyl-N'-[4-[2-(6-methyl-(2-pyridyl)ethoxy]phenyl]urea (Compound No. 1) as colorless crystals, mp 113° to 114° C.

IR(nujol) $\nu_{max}^{cm-1}$: 3360, 1635, 1510, 1230, 815.

NMR(CDCl₂) δ, ppm: 2.56(3H,s), 2.96(6H,s), 3.23(2H,t), 4.34(2H,t), 6.43(1H,broad s), 6.91(2H,d), 7.31(2H,d), 7.07 to 7.72 (3H,m).

Elemental Analysis, for $C_{17}H_{21}N_3O_2$: Calcd. (%): C, 68.20; H, 7.07; N, 14.04. Found (%): C, 68.30; H, 6.95; N, 13.93.

EXAMPLE 2

N,N-dimethyl-N'-[4-[2-(5-ethyl-2-pyridyl)ethoxy]-phenyl]urea

By a procedure analogous to that employed in Example 1, from 6.0 g of 4-[2-(5-ethyl-2-pyridyl)ethoxy]aniline is obtained 5.8 g of N,N-dimethyl-N'-[4-[2-(5-ethyl-2-pyridyl)ethoxy]phenyl]urea (Compound No. 2) as colorless crystals, mp 121° to 122° C.

IR(nujol) $\nu_{max}^{cm-1}$: 3290, 1640, 1515, 1240, 815.

NMR(CDCl₃) δ, ppm: 1.18(3H,t). 2.59(2H,q), 2.90(6H,s), 3.14(2H,t), 4.27(2H,t), 6.27(1H,broad s), 6.80(2H,d), 7.20(2H,d), 7.07 to 7.53 (2H,m), 8.37(1H,d).

Elemental analysis, for $C_{18}H_{23}N_3O_2$: Calcd (%): C, 68.98; H, 7.40; N, 13.41. Found (%): C, 69.20; H, 7.34;N, 13.35.

EXAMPLE 3

N-methoxy-N-methyl-N'-[4-[2-(6-methyl-2-pyridyl)ethoxy]phenyl]urea (a) To 10 ml of tetrahydrofuran is added 1 g of 1,1'-carbonyldiimidazole. To the mixture is added, while stirring at 5° to 6° C., a solution of 1 g of 4-[2-(6-methyl-2-pyridyl)ethoxy]aniline in 4 ml of dichloromethane.

The mixture is stirred at 10° C. for ten minutes and at 18° C. for fifteen minutes. To the resultant is added 0.31 g of methylmethoxyamine at 12° to 14° C., followed by stirring at 15° C. for 10 minutes and at 20° C. for 1 hour. The reaction mixture is subjected to filtration, and the filtrate is concentrated, and the resulting crystals are washed with a 5% aqueous solution of sodium hydrogen carbonate and with water. The crystals are dried and recrystallized from a mixture of isopropyl ether and dichloromethane to yield 1.1 g (85.3% yield) of N-methyl-N-methoxy-N'-[4-[2-(6-methyl-2-pyridyl)ethoxy]phenyl]urea as colorless crystals (Compound No. 3), mp 96° to 97° C.

IR(nujol) $\nu_{max}^{cm-1}$: 3250, 1670.

NMR(CDCl₃) δ, ppm: 2.55(s,3H), 3.18(s,3H), 3.20(t,2H), 3.80(s,3H), 4.37(t,2H), 6.85 to 7.75 (m,8H).

Elemental Analysis, for $C_{17}H_{21}N_3O_3$: Calcd. (%): C, 64.74; H, 6.71; N, 13.32. Found (%): C, 64.97; H, 6.83; N, 13.43.

(b) To a solution of 1.2 g of 4-[2-(6-methyl-2-pyridiyl)ethoxy]aniline and 0.8 g of pyridine in 30 ml of chloroform is added, at temperatures of from −10° C. to −5° C., 5 g of 10% phosgene solution in toluene.

The mixture is then stirred for 30 minutes at −5° C., followed by dropwise addition of chloroform solution containing 0.45 g of methylmethoxyamine. The temperature is raised gradually, and the mixture is stirred for 30 minutes at 10° C. and then for one hour at 20° C. The reaction solution is washed with a 5% aqueous solution of sodium hydrogen carbonate, then with water. The thus washed solution is dried over anhydrous sodium sulfate, followed by concentration. The residue is recrystallized from a mixture of isopropyl ether and dichloromethane to yield 1.1 g of N-methoxy-N-methyl-N'-[4-[2-(6-methyl-2-pyridyl)ethoxy]phenyl]urea (Compound No. 3), mp 96° to 97° C. IR(nujol) $\nu_{max}^{cm-1}$: 3250, 1670

EXAMPLE 4

N'-[4-[2-(5-ethyl-2-pyridyl)ethoxy]phenyl]-N-methoxy-N-methylurea

By a procedure analogous to that employed in Example 3(a) is obtained N'-[4-[2-(5-ethyl-2-pyridyl)ethoxy]phenyl]-N-methoxy-N-methylurea (Compound No. 4) as colorless crystals, mp 90.5° to 92° C.

IR(nujol) $\nu_{max}^{cm-1}$: 3200, 1670.

NMR(CDCl₃) δ, ppm: 1.23(t,3H), 2.65(q,2H), 3.17(s,3H), 3.20(t,2H), 3.75(s,3H), 4.35(t,2H), 6.82-7.80(m,7H), 8.47(d,1H).

Elemental Analysis, for $C_{18}H_{23}N_3O_3$ Calcd. (%): C, 65.63; H, 7.04; N, 12.76. Found (%): C, 65.72; H, 6.98; N, 12.75.

EXAMPLE 5

N,N-dimethyl-N'-[4-[2-(5-methyl-2-pyridyl)ethoxy]-phenyl]urea

By a procedure analogous to that employed in Example 1, from 1.5 g of 4-[2-(5-methyl-2-pyridyl)ethoxy]aniline is obtained 0.78 g of N,N-dimethyl-N'-[4-[2-(5-methyl-2-pyridyl)ethoxy]phenyl]urea (Compound No. 5) as colorless crystals, mp 148° to 150° C.

IR(nujol) $\nu_{max}^{cm-1}$: 3310, 1640.

NMR(CDCl₃) δ, ppm: 2.22(3H,s), 2.85(6H,s), 3.10(2H,t). 4.15(2H,t), 6.50 to 8.26(8H,m).

Elemental Analysis, for $C_{17}H_{21}N_3O_2$: Calcd. (%): C, 68.20; H, 7.07; N, 14.04. Found (%): C, 68.15; H, 6.75; N, 13.65.

EXAMPLE 6

N,N-dimethyl-N'-[4-[2-(4-methyl-2-pyridyl)ethoxy]-phenyl]urea

By a procedure analogous to that employed in Example 1, from 1.5 g of 4-[2-(4-methyl-2-pyridyl)ethoxy]aniline is obtained 0.45 g of N,N-dimethyl-N'-[4-[2-(4-methyl-2-pyridyl)ethoxy]phenyl]urea (Compound No. 6) as colorless crystals, mp 132° to 133° C.

IR(nujol) $\nu_{max}^{cm-1}$: 3305, 1640.

NMR(CDCl$_3$) δ, ppm: 2.45(3H,s), 3.13(6H,s), 3.40(2H,t), 4.59(2H,t), 6.73 to 9.16(8H,m).

Elemental Analysis, for $C_{17}H_{21}N_3O_2$: Calcd. (%): C, 68.20; H, 7.07; N, 14.04. Found (%): C, 68.16; H, 6.78; N, 13.86.

EXAMPLE 7

N,N-dimethyl-N'-[4-[2-(3-methyl-2-pyridyl)ethoxy]-phenyl]urea

By procedure analogous to that employed in Example 1, from 2.6 g of 4-[2-(3-methyl-2-pyridyl)ethoxy]aniline is obtained 1.8 g of N,N-dimethyl-N'-[4-[2-(3-methyl-2-pyridyl)ethoxy]phenyl]urea (Compound No. 7) as colorless crystals, mp 123° to 125° C.

IR(nujol) $\nu_{max}^{cm-1}$: 3300, 1640.

NMR(CDCl$_3$) δ, ppm: 2.42(3H,s), 3.03 (6H,s), 3.37(2H,t), 4.57(2H,t), 7.05–8.00(7H,m), 8.85–8.98(1H,m).

Elemental Analysis, for $C_{17}H_{21}N_3O_2$: Calcd. (%): C, 68.20; H, 7.07; N, 14.04. Found (%): C, 68.12; H, 7.11; N, 14.03.

EXAMPLE 8

N,N-dimethyl-N'-[4-[2-(4,6-dimethyl-2-pyridyl)ethoxy]phenyl]urea

By a procedure analogous to that employed in Example 1, from 1.8 g of 4-[2-(4,6-dimethyl-2-pyridyl)ethoxy]aniline is obtained 1.6 g of N,N-dimethyl-N'-[4-[2-(4,6-dimethyl-2-pyridyl)ethoxy]phenyl]urea (Compound No. 8) as colorless crystals, mp 113° to 114° C.

IR(nujol) $\nu_{max}^{cm-1}$: 3280, 1640.

NMR(CDCl$_3$) δ, ppm: 2.21(3H,s), 2.43(3H,s), 2.87(6H,s), 3.09(2H,t), 4.16(2H,t), 6.55(1H,br.s), 6.56 to 7.36(6H,m).

Elemental Analysis, for $C_{18}H_{23}N_3O_2$: Calcd. (%): C, 68.98; H, 7.40; N, 13.41. Found (%): C, 69.21; H, 7.42; N, 13.47.

EXAMPLE 9

N-methoxy-N-methyl-N'-[4-[2-(5-methyl-2-pyridyl)ethoxy]phenyl]urea

By a procedure analogous to that employed in Example 3(a), from 1.5 g of 4-[2-(5-methyl-2-pyridyl)ethoxy]aniline is obtained 1.65 g of N-methoxy-N-methyl-N'-[4-[2-(5-methyl-2-pyridyl)ethoxy]phenyl]urea (Compound No. 9) as colorless crystals, mp 110° to 112° C.

IR(nujol) $\nu_{max}^{cm-1}$: 3420, 1675.

NMR(CDCl$_3$) δ, ppm: 2.21(3H,s), 3.09(3H,s), 3.15(2H,t), 3.60(3H,s), 4.24(2H,t), 6.70 to 8.40(8H,m).

Elemental Analysis, for $C_{17}H_{21}N_3O_3$: Calcd. (%): C, 64.74; H, 6.71; N, 13.32. Found (%): C, 64.38; H, 6.48; N, 13.03.

EXAMPLE 10

25 g of Compound No. 1, 5 g of a surface-active agent of polyoxyethylene ether type and 70 g of talc are sufficiently crushed and mixed to prepare a wettable powder.

EXAMPLE 11

10 g of Compound No. 1, 20 g of a surface-active agent of polyethylene glycol ether type and 70 g of cyclohexanone are sufficiently mixed to prepare an emulsifiable concentrate.

EXAMPLE 12

5 g of Compound No. 3, 40 g of bentonite, 50 g of clay and 5 g of sodium lignin sulfonate are sufficiently crushed and mixed, which is sufficiently kneaded with addition of water, followed by granulation and drying to provide a granular preparation.

EXAMPLE 13

3 g of Compound No. 2 and 97 g of clay are sufficiently crushed and mixed to provide a powdery preparation.

TEST EXAMPLE 900 cm$^2$-Plastic pots are packed with crop-filed soil and sown with seeds of Red root pigweed (*Amaranthus retroflexus* L.), Purple lambsquarter (*Chenopodium album* (L.) var. *centrorubrum* Makino), Oriental smartweed, (*Polygonum Blumei* Meisn.), Common purslane (*Portulaca oleracea* L.), Tall morningglory (*Ipomoea purpurea* (L.) Roth), Cocklebur (*Xanthium strumarium* L.), Velvetleaf (*Abutilon theophrasti* Medic.), Jimson weed (*Datura stramonium* L.) and Corn (*Zea mays* L.)

These test plants are grown in a greenhouse for 9–14 days. When the true leaves sprouted, these pots are placed in a chamber of 1000 cm$^2$, where 10 ml each of solutions each containing a given weight of the test compound is applied to each plant from the above with a small spraygun so that each drug solution is applied to leaves and stalks of the respective plants homogeneously. These pots are then left standing in the greenhouse for 14 days. Then, the above-ground portions of each of the thus treated plants, which have remained non-withering, are collected by cutting, followed by weighing while they are fresh.

The non-withering ratio is calculated on the basis of the corresponding weight of the control (non-treated) plants as 100%. The phytotoxicity and herbicidal effect of the test compound are evaluated on the basis of the following criteria. The test solution is prepared by dissolving the test compound of a given weight in 1 ml of acetone containing 1% of a surface-active agent, Tween 20 ® (Kao Atlas Co., Japan), which is diluted with deionized water to make the total volume to be 10 ml.

To dissolve or disperse the test compound completely in the acetone, stirring by means of super-sonic wave is employed.

The herbicidal effects are indicated with the following indexes:

| Index | Effect | Inhibition (Herbicidal) (%) |
|---|---|---|
| 0 | No effect | 0 |
| 1 | Slightly effective | 0.1 to 50 |
| 2 | Somewhat effective | 50.1 to 70 |

| Index | Effect | Inhibition (Herbicidal) (%) |
|---|---|---|
| 3 | Moderately effective | 70.1 to 87.5 |
| 4 | Highly effective | 87.6 to 99.9 |
| 5 | Exceedingly effective | 100% |

Phytotoxicity to crop (corn) is indicated with the following indexes:

| Index | Phytotoxicity | Percentage of damage (%) |
|---|---|---|
| 0 | None | 0 |
| 1 | Negligible | 0.1 to 12.5 |
| 2 | Slight | 12.6 to 30 |
| 3 | Medium | 30.1 to 50 |
| 4 | Serious | 50.1 to 99.9 |
| 5 | Maximal | 100 |

(The indexes 0 and 1 to crop denote the test compound can be practically applicable to crop.)

The results are shown in the following table.

TABLE

| Compound No. | Application rate | Herbicidal effect | | | | | | | | Phyto-toxicity Corn |
|---|---|---|---|---|---|---|---|---|---|---|
| | | Red root pigweed | Purple lambs-quarter | Oriental smart-weed | Common purslane | Tall morning-glory | Cock-lebur | Vel-vetleaf | Jimson weed | |
| 1 | 10 | 5 | 5 | 4 | 2 | 5 | 5 | 5 | 5 | 0 |
|   | 20 | 5 | 5 | 5 | 5 | 5 | 5 | 5 | 5 | 0 |
| 2 | 10 | 5 | 5 | 4 | 5 | 5 | 5 | 5 | 5 | 1 |
|   | 20 | 5 | 5 | 5 | 5 | 5 | 5 | 5 | 5 | 1 |
| 3 | 10 | 5 | 5 | 3 | 5 | 4 | 4 | 5 | 5 | 1 |
|   | 20 | 5 | 5 | 3 | 5 | 4 | 5 | 5 | 5 | 1 |

What is claimed is:

1. A compound of the general formula:

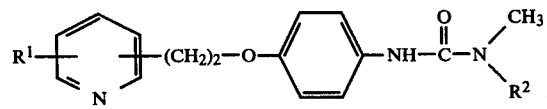

wherein $R^1$ stands for a lower alkyl group; and $R^2$ stands for a lower alkyl group or a lower alkoxy group, or a salt thereof.

2. A compound as claimed in claim 1, which is N,N-dimethyl-N'-[4-[2-(5-ethyl-2-pyridyl)ethoxy]phenyl-]urea.

3. A compound as claimed in claim 1, which is N'-[4-[2-(5-ethyl-2-pyridyl)ethoxy]phenyl]-N-methoxy-N-methylurea.

4. A compound as claimed in claim 1, which is N,N-dimethyl-N'-[4-[2-(6-methyl-2-pyridyl)ethoxy]phenyl-]urea.

5. A herbicide containing an effective amount of a compound of the general formula:

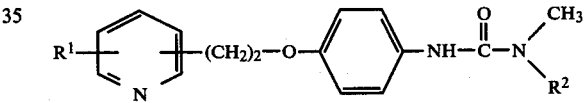

wherein $R^1$ stands for a lower alkyl group; and $R^2$ stands for a lower alkyl group or a lower alkoxy group, or a salt thereof, and an inert carrier therefor.

* * * * *